United States Patent [19]

Golunski et al.

[11] Patent Number: 5,593,935
[45] Date of Patent: Jan. 14, 1997

[54] CATALYSTS

[75] Inventors: Stanislaw E. Golunski; John W. Hayes, both of Reading, United Kingdom

[73] Assignee: Johnson Matthey Public Limited Company, London, England

[21] Appl. No.: 283,569

[22] Filed: Aug. 1, 1994

[30] Foreign Application Priority Data

Aug. 14, 1993 [GB] United Kingdom .................. 9316955

[51] Int. Cl.⁶ .......................... B01N 23/00; B01N 23/40; B01N 23/42
[52] U.S. Cl. .......................... 502/339; 502/325; 502/349; 502/352
[58] Field of Search .................... 502/325, 339, 502/349, 352

[56] References Cited

U.S. PATENT DOCUMENTS

| | | |
|---|---|---|
| 3,511,888 | 5/1970 | Jenkins . |
| 3,670,044 | 6/1972 | Drehman et al. . |
| 3,745,112 | 7/1973 | Rausch . |
| 3,790,473 | 2/1974 | Rausch . |
| 3,864,284 | 2/1975 | Clippinger et al. . |
| 3,939,220 | 2/1976 | Rausch ................................. 585/379 |
| 3,998,900 | 12/1976 | Wilhelm . |
| 4,003,826 | 1/1977 | Antos . |
| 4,003,852 | 1/1977 | Hayes . |
| 4,032,589 | 6/1977 | Wall . |
| 4,152,246 | 5/1979 | Weisang et al. . |
| 4,431,750 | 2/1984 | McGinnis et al. ...................... 502/329 |
| 4,486,547 | 12/1984 | Imai et al. . |
| 4,788,371 | 11/1988 | Imai et al. . |
| 4,902,848 | 2/1990 | Scott et al. . |
| 4,914,075 | 4/1990 | Bricker et al. . |
| 4,926,005 | 5/1990 | Olbrich et al. . |
| 5,113,023 | 5/1992 | Anderson . |
| 5,128,300 | 7/1992 | Chao et al. . |
| 5,220,091 | 6/1993 | Brinkmeyer et al. . |
| 5,283,041 | 2/1994 | Nguyen et al. .......................... 502/325 |

FOREIGN PATENT DOCUMENTS

| | | |
|---|---|---|
| 0228792 | 7/1987 | European Pat. Off. . |
| 2024263 | 1/1980 | United Kingdom . |

OTHER PUBLICATIONS

Inside front cover of the CRC Handbook of Chemistry and Physics, 60th edition, CRC Press 1980 (Periodic Table of the Elements).

*Primary Examiner*—Anthony McFarland
*Assistant Examiner*—E. D. Irzinski
*Attorney, Agent, or Firm*—Watson Cole Stevens Davis, P.L.L.C.

[57] ABSTRACT

The dehydrogenation of an alkane to an alkene, especially isobutane to isobutene, is carried out in admixture with oxygen and in the absence of added steam over a dehydrogenation and oxidation catalyst comprising a platinum group metal deposited upon a support. A catalyst comprising platinum deposited on a support which is a mixture of tin oxide and zirconium oxide possesses good activity for the dehydrogenation of an alkane, especially carried out in this way.

11 Claims, 2 Drawing Sheets

CATALYSTS

The present invention concerns improvements in catalysts and in catalytic processes. More especially it concerns catalysts and processes for dehydrogenation of alkanes.

It is known to dehydrogenate isobutane to isobutene using direct dehydrogenation at low space velocity (GHSV= 100–1000 hr$^{-1}$). The conventional industrial process has several inherent disadvantages:

(a) it is an endothermic reaction, requiring high thermal input;

(b) the yield of isobutene is equilibrium limited; and (c) at temperatures favouring high yields of isobutene, the rate of catalyst de-activation is also high.

Improvements to the conventional process have included the addition of either steam (eg U.S. Pat. No. 4,926,005 and 4,788,371) or hydrogen (eg U.S. Pat. No. 4,032,589) to the gas feed. The function of the hydrogen is as a diluent, and to reduce the deposition of carbon on the catalyst. The steam improves thermal conduction through the catalyst bed and reduces the deposition of carbon on the catalyst, and hence it too has been used as a diluent. The catalysts used in industry include platinum on alumina, platinum on tin oxide and chromium oxide-based catalysts. There remains a need for an improved process for the dehydrogenation of alkanes, especially for the dehydrogenation of isobutane, which is a starting material for MTBE (methyl-tert-butyl-ether) production. The conventional processes require high inputs of energy and the capital cost of a catalytic reactor designed to supply large amounts of heat is particularly high. Moreover, conventional processes demonstrate rapid catalyst deactivation, so that expensive and complex catalyst regeneration has to be designed into the equipment and the process.

The present invention provides an improved process and novel catalyst for alkane dehydrogenation.

Accordingly, the invention provides a process for the dehydrogenation of an alkane to form an alkene, comprising passing a feedstock comprising said alkane in the gas phase in admixture with oxygen and in the absence of added steam over a dehydration and oxidation catalyst comprising a platinum group metal deposited upon a support.

The invention provides also a catalyst for alkane dehydrogenation, comprising platinum deposited upon a support which is a mixture of tin oxide and zirconium oxide. The invention also provides a process for the dehydrogenation of an alkane to form an alkene, comprising passing a feedstock comprising said alkane in the gas phase over this catalyst.

The present processes and catalyst are advantageous over the known processes and catalyst by reason of one or more of such features as higher yield of the alkene, higher selectivity to the alkene, lower operating temperature, lower heat input, a simpler system and lower catalyst deactivation.

There is much prior art on the dehydrogenation of alkanes to alkenes, (though a scant amount on the oxidative dehydrogenation of alkanes to alkenes), yet the present improvements were not realised before. As explained in the U.S. specification 4,788,371 mentioned above, the dehydrogenation of hydrocarbons is endothermic. In a system employing a dehydrogenation catalyst only, it is typically necessary to add superheated steam at various points in the process or to intermittently remove and reheat the reaction stream between catalyst beds. In an improvement, processes were developed which utilised a two-catalyst system with distinct beds or reactors of dehydrogenation or selective oxidation catalysts. The purpose of the selective oxidation catalysts was to selectively oxidise the hydrogen produced as a result of the dehydrogenation with oxygen that had been added to the oxidation zone to generate heat internally in the process. The heat generated would typically be sufficient to cause the reaction mixture to reach desired dehydrogenation temperatures for the next dehydrogenation step. The US specification explains that in its invention one specific catalyst can be used to accomplish both the dehydrogenation and oxidation reactions. It discloses a process for the steam dehydrogenation of a dehydrogenatable hydrocarbon with oxidative reheating which comprises contacting a dehydrogenatable hydrocarbon comprising $C_2$–$C_{15}$ paraffins and steam at a steam to hydrocarbon molar ratio of from 0.1:1 to 40:1, at a pressure from 0.1 to 10 atmospheres, a temperature of from 400° to 900° C., and a liquid hourly space velocity of from 0.1 to 100 hr$^{-1}$ with a catalyst in the first reaction zone of a reactor containing a plurality of reaction zones and introducing an oxygen-containing gas into the second, and every other reaction zone of the plurality of reaction zones such that the total rate of the oxygen-containing gas introduced into the reaction zone ranges from 0.01 to 2 moles of oxygen per mole of $C_2$–$C_{15}$ paraffin feed wherein the catalyst is comprised of from 0.1 to 5 weight % platinum, and from 0.01 to 5 weight% potassium or cesium or mixtures thereof on an alumina support having a surface area of from 5 to 120 m$^2$/g and recovering the products of the reaction. Though the specification mentions the possibility of a single reaction zone within a single reactor with single inlet and outlet parts, all co-feeds entering the inlet of the reactor and products and by-products leaving the system through the reactor outlet part, there is no Example illustrating this concept. Moreover, the present broad process involving passing an alkane in admixture with oxygen over a dehydrogenation and oxidation catalyst is not a steam dehydrogenation; instead, it is carried out in the absence of added steam (though some steam is formed by reaction of the oxygen with hydrogen which is present). In this aspect of the present invention, we have discovered that oxygen in the absence of added steam is advantageously admixed with the alkane and passed over the catalyst, so that heat produced by the exothermic reaction of the oxygen with hydrogen which is present provides, partially or fully, the heat required by the endothermic dehydrogenation. The hydrogen required for the reaction with the oxygen can be introduced into the reaction zone, but this is not preferred. Advantageously, the hydrogen is hydrogen produced by the dehydrogenation of the alkane to alkene, so as to shift the equilibrium in favour of the alkene. Preferably, the amount of oxygen is such that the dehydrogenation is carded out under adiabatic conditions, so that no heat is supplied (or removed) from the reaction. Especially preferred is the amount of oxygen being such that the endothermic dehydrogenation is balanced by the exothermic reaction of the oxygen with hydrogen which is present so that the temperature remains constant (this situation is referred to herein as thermally neutral conditions). Thus, the optimum temperature for yield, life of catalyst etc can be maintained, eg so that at least 95% selectivity to the alkene is obtained.

The amount of oxygen is desirably less than the amount of the alkane, on a molar basis, and preferably less than half the amount of the alkane on this basis. For example, employing isobutane as the alkane, it is preferred that the amount of oxygen be below that indicated by the stoichiometry of the reaction equation:

$$C_4H_{10} + 0.5O_2 \rightarrow C_4H_8 + H_2O.$$

The optimum amount of oxygen will vary with the desired operating temperature, and as a guide we would predict that the maximum amount of oxygen for highly selective, thermally neutral, dehydrogenation of isobutane be 5% at 450° C., 7.5% at 500° C. and 9% at 550° C., based on the combined volumes of isobutane and oxygen.

The present oxidative dehydrogenation is usually carried out at a temperature from 350° to 550° C., for instance at a temperature from 350° to 480° C., for example when the platinum group metal comprises platinum and the support comprises alumina.

The oxidative dehydrogenation is preferably carried out under relatively high space velocities, such as an alkane, and especially a total, gas hourly space velocity (GHSV) of 1000 to 5000 hr$^{-1}$, for example for isobutane.

The operating pressure is conveniently atmospheric, but the dehydrogenation can be operated at above or below atmospheric pressure. If desired, diluent gases can be used, although hydrogen is not recommended as explained above; in addition, it would be an added process cost.

The alkane which is dehydrogenated is preferably raw material, not alkane which has already been partially dehydrogenated.

The oxygen can be employed as such but conveniently it is employed as a component of an oxygen-containing gas, particularly air.

The platinum group metal dehydrogenation and oxidation catalyst can be such a catalyst known in the art. The platinum group metal (ruthenium, rhodium, palladium, osmium, iridium and platinum) is preferably platinum. The catalyst preferably contains 0.1 to 3% by weight of the platinum group metal, eg platinum. The support can be for example alumina, silica, magnesia, titania, zirconia or a mixture or joint oxide (eg an alumina silicate) thereof, or a Group IIA or IIB (eg zinc) aluminate spinel. Groups IIA and IIB are as given in the inside front cover of the CRC Handbook of Chemistry and Physics, 60th edition, CRC Press, 1980. Commonly, the support comprises (ie consists of or includes) alumina. For instance, the catalyst contains as support 10–99.9% by weight of alumina. Promoters can be employed with the platinum group metal. Preferred as promoter is tin oxide. The promoter, when present, is usually employed as 0.1–5% by weight of the catalyst. The catalyst can be obtained in conventional ways, for example by impregnating the support with a precursor of the platinum group metal and a precursor of any co-promoter, and calcining.

A particularly advantageous catalyst for the present oxidative dehydrogenation of an alkane in the absence of added steam, though it can be used advantageously for the oxidative dehydrogenation in the presence of added stem, and indeed for the direct dehydrogenation, is a novel catalyst. This catalyst for alkane dehydrogenation comprises platinum deposited upon a support which is a mixture of tin oxide and zirconium oxide. The catalyst contains a catalytically effective amount of the platinum. Usually the catalyst contains 0.1 to 3% by weight of platinum, calculated as metal. Additional catalytically active components can be present, though preferably the catalytically active component consists essentially of platinum. The catalyst contains a supporting amount of the mixture of tin oxide and zirconium oxide. Additional support components can be present. The common support component alumina, however, has been found to be disadvantageous. Preferably, therefore, the catalyst contains substantially no alumina. It is preferred that the support consists essentially of the mixture of tin oxide and zirconium oxide. Usually the catalyst contains 6–60, preferably 10–60, especially 15–30, % by weight of the tin oxide (measured as tin oxide). Usually the catalyst contains 37–94.9, preferably 70–85, % by weight of the zirconium oxide. The weight ratio of the tin oxide to the zirconium oxide is preferably 1:3–9, especially 1:3–5. In a preferred embodiment, the catalyst comprises 0.1 to 3% by weight of platinum, calculated as metal, 10 to 60% by weight of tin oxide, the balance being zirconium oxide. A particular catalyst has a support comprising $SnO_2$ and $ZrO_2$ in a weight ratio of approximately 1:4. One preferred embodiment of the catalyst of the invention is prepared by impregnating 1% (by weight, calculated as metal) of a platinum salt or compound onto a co-precipitate of $SnO_2$ and $ZrO_2$ in a weight ratio of 1:4.

The catalyst of the invention may comprise in addition other components such as promoters and/or stabilisers. The catalyst may be in the form of pellets or other shapes, for example produced by pelletisation or extrusion, or may be supported on high surface area monoliths such as ceramic or metal honeycomb monoliths.

The mixture of $SnO_2$ and $ZrO_2$ may be formed in a variety of ways and there may be a chemical interaction or compound formation between the components which is as yet not fully understood. The preferred method of preparation is by co-precipitation; suitably by adding NaOH to a mixture of tin and zirconium salts in aqueous solution. The mixture may then be dried and calcined, especially to yield a powdered material with moderately high surface area (typically 95 $m^2g^{-1}$) and narrow pore-size distribution (most of the pores having a radius of about 2 nm), before impregnation with an aqueous solution of a platinum salt. The impregnated catalyst is suitably dried and calcined again.

The invention further provides a process for the dehydrogenation of alkanes to form alkenes, comprising passing a feedstock comprising said alkane in the gas phase over a catalyst according to the invention. Advantages of the present catalyst and process are indicated in the Examples hereafter. In particular, the invention provides the use of the catalyst in the oxidative dehydrogenation of an alkane, whereby extended durability before regeneration is achieved.

The process employing the novel catalyst is particularly advantageous when operated as an oxidative dehydrogenation reaction. That is, the invention includes a process for the oxidative dehydrogenation of alkanes to form alkenes, comprising passing a feedstock comprising said alkane in the gas phase in admixture with oxygen over a catalyst according to the invention. The oxygen can be employed as such, but conveniently it is employed as a component of an oxygen-containing gas, particularly air.

The oxidative dehydrogenation using the novel catalyst can be carried out *mutatis mutandis* as described above for oxidative dehydrogenation in the absence of added steam using catalysts in general. For instance, the oxidalive dehydrogenation, with or without added steam, using the novel catalyst is preferably carded out under relatively high space velocities, such as an alkane, and preferably a total, GHSV of 1000 to 5000 hr$^{-1}$, for example for isobutane.

Preferably, the oxidative dehydrogenation using the novel catalyst is operated under adiabatic conditions, especially thermally neutral conditions. The amount of free oxygen in the feedstock is preferably, therefore, controlled to achieve this under the other operating conditions chosen. In particular, the amount of oxygen required increases with increasing temperature. It has been found that operation under adiabatic conditions offers the opportunity to overcome many of the disadvantages of direct dehydrogenation. In preferred embodiments, the process of the invention:

i) provides heat within the catalyst bed by reacting exothermically with some of the hydrogen being formed;

ii) by consuming hydrogen, can shift the equilibrium in favour of the desired products; and iii) suppresses two of the major causes of catalyst deactivation, that is over-reduction of the catalyst and carbon deposition.

The concentration of oxygen should be carefully controlled at adiabatic conditions, and it is believed that the amount of oxygen should be maintained below stoichiometric relative to the amount of hydrogen present. There are two primary reasons for requiring that the amount of oxygen be carefully controlled, firstly to avoid unwanted products being produced, either from partial or deep oxidation, and secondly to prevent excessive temperature excursions caused by large exotherms.

Desirably, the oxidative dehydrogenation reaction using the novel catalyst is carried out at a temperature of from 350° to 550° C., more preferably in the range 400° to 530° C., especially 440° to 510° C. The operating pressure is conveniently atmospheric, but the process may be operated at above or below atmospheric pressure. If desired, diluent gases may be used, although hydrogen is not recommended since it would be consumed and be an added process cost.

Although the present invention, whether involving the novel catalyst or not, is described herein with particular reference to the oxidative dehydrogenation of isobutane, the invention should not be considered as limited thereto, and may be applied to alkanes in general, and the novel catalyst may also find application in direct dehydrogenation. Nonetheless, it is believed that the greatest benefits arise in oxidative dehydrogenation. The alkane is usually of 2–15, preferably 2–5, particularly 3 or 4, carbon atoms. The alkane can be linear, though preferably it is branched.

BRIEF DESCRIPTION OF THE DRAWINGS

The invention is illustrated by the accompanying two drawings FIGS. 1 and 2, which each represent two graphs showing yield data and which are described in the Examples hereafter.

The invention will now be described with reference to the following Examples.

Figure 1:
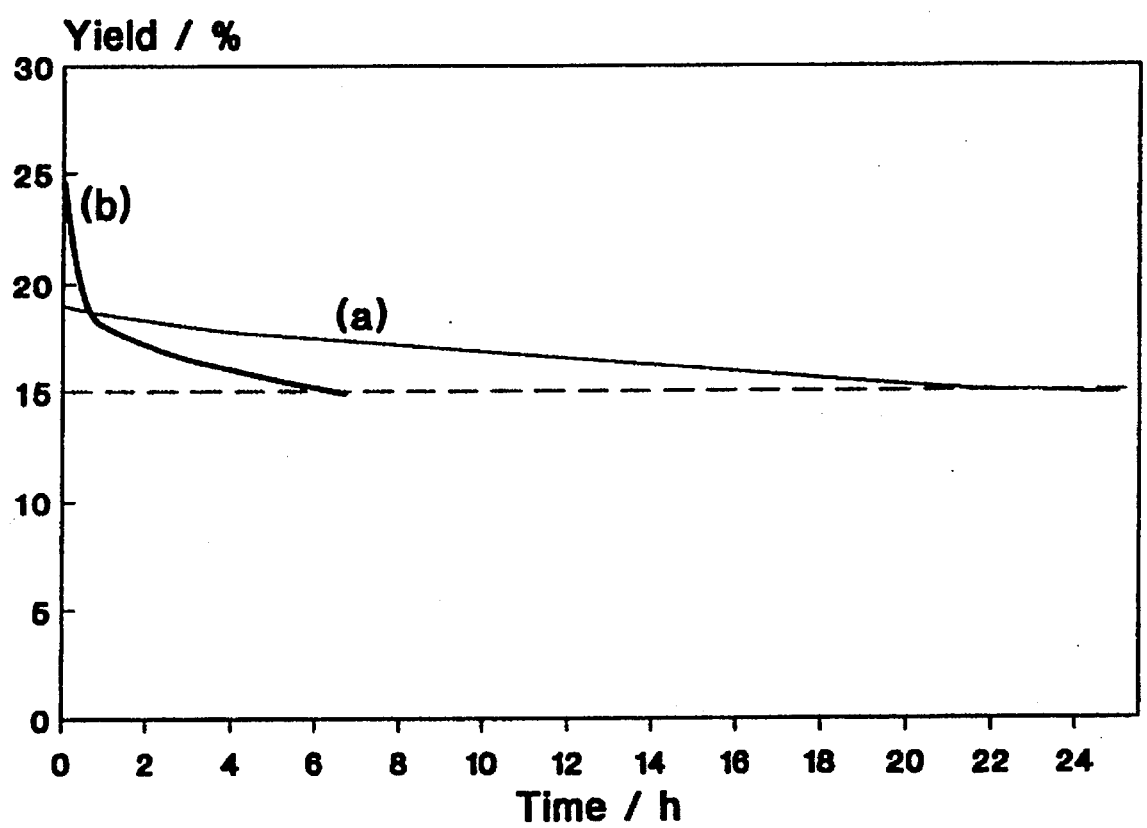

In the prior art, the Pt and Sn are usually supported on $Al_2O_3$, with the loading of Sn being ≤5% measured as tin (see J C Hayes, U.S. Pat. No. 4,003,852). Although there are some references to the use of $ZrO_2$ (E Clippinger and B F Mulaskey, U.S. Pat. No. 3,864,284; G J Antos, U.S. Pat. No. 4,003,826; J C Hayes, U.S. Pat. No. 4,003,852), its function has been claimed to be simply that of a physical support.

EXAMPLE 1 AND COMPARATIVE EXAMPLE 1

Pt-Sn/$Al_2O_3$ is a known hydrocarbon-conversion catalyst, which is effective for reactions such as reforming (see T-H Chao et al U.S. Pat. No. 5,128,300) and direct dehydrogenation (see J W Jenkins, U.S. Pat. No. 3,511,888) of $C_2$–$C_{20}$ alkanes. A catalyst with the nominal composition (by mass) of 1%Pt-1%Sn/$Al_2O_3$ was prepared (following the method described by F C Wilhelm, U.S. Pat. No. 3,998,900) by co-impregnating $\gamma$-$Al_2O_3$ with an aqueous mixture of hydrogen hexachloroplatinate(IV) (chloroplatinic acid) and acidified tin(II) chloride. The resultant material was dried (110° C.; air;, 24 hr) and calcined (500° C.; air; 2 hr). As is conventional, small amounts of tin oxide are measured and written as Sn and larger amounts, eg 10%, are measured and written as $SnO_2$.

A packed bed (1 $cm^3$) of powdered sample (<150 µm particle diameter) was tested in an adiabatic reactor. For measurements of direct-dehydrogenation activity at 450° C., in Comparative Example 1, a gas-feed of undiluted isobutane was used at a flow-rate of 50 $cm^3$ $min^{-1}$ (GHSV=3000 $hr^{-1}$; MHSV=6 $dm^3$ $hr^{-1}g_{cat}^{-1}$). The molar conversion (% isobutane converted to all products) and selectivity (number of moles of isobutane converted to isobutene divided by number of moles of isobutane converted to all products) were recorded as a function of time at selected furnace/gas-inlet temperatures; the molar yield was calculated from the relationship:

$$Yield/\% = \frac{conversion/\% \times selectivity/\%}{100}$$

Oxidative dehydrogenation was carded out, in Example 1, by adding just enough air to the gas-feed to ensure thermally-neutral operation (ie, bed temperature=furnace/gas-inlet temperature). The space velocity of the isobutane was the same, therefore, as during direct dehydrogenation. Again, the molar conversion and selectivity were recorded as a function of time.

In both modes of operation (direct dehydrogenation and oxidative dehydrogenation), the catalyst showed very high selectivity (≧95%) toward isobutene formation. Only during the first 5 minutes of testing was there any sign of an undesired cracking product (propene). In the oxidative mode, the amount of $CO_2$ formed was just above the detection limit of the GC analyser, no CO was detected.

As shown in Table 1, the direct-dehydrogenation activity declined noticeably during the first 60 minutes; thereafter, the de-activation was very gradual. The initial loss in activity coincided with the bed temperature decreasing to a new stable value, as the endothermic reaction reached steady-state.

TABLE 1

(Comparative Example 1)
Direct Dehydrogenation over 1% Pt—1% Sn/$Al_2O_3$

| Elapsed Time/min | Isobutene Yield/% 450° C. |
| --- | --- |
| 2 | 16.3 |
| 25 | 15.4 |
| 55 | 15.2 |
| 120 | 15.1 |
| 300 | 14.7 |
| 1800 | — |

—: not recorded

When the catalyst was tested in the oxidalive mode, at 450° C. and 500° C., the reaction became thermally neutral when the oxygen concentration reached ca 3 or 4% at 450° C., and ca 5.5% at 500° C. The initial activity at 450° C. was higher than for direct dehydrogenation (compare Tables 1 and 2). The isobutene yield is higher at 500° C. than at 450° C.

TABLE 2

(Example 1)
Oxidative dehydrogenation over 1% Pt—1% Sn/Al$_2$O$_3$

| Elapsed Time/min | Isobutene Yield/% | |
| --- | --- | --- |
| | 450° C. | 500° C. |
| 2 | 24.6 | 27.8 |
| 25 | 18.7 | 24.6 |
| 55 | 18.0 | 23.0 |
| 100 | — | 21.6 |
| 180 | 16.4 | 19.2 |
| 300 | 15.5 | 16.5 |
| 400 | 14.9 | — |

EXAMPLE 2

The catalyst described in Example 1 and Comparative Example 1 was used to dehydrogenate isobutane at 450° C., under the conditions described in Comparative Example 1. The yield of isobutene was allowed to decline to 15%, before air was added to the gas-feed. The activity of the catalyst was then measured as a function of gas-feed composition (Table 3).

TABLE 3

Oxidative dehydrogenation of isobutane over 1% Pt—1% Sn/Al$_2$O$_3$ at 450° C.

| % Air in Gas-Feed | Bed Temperature °C. | Isobutane Conversion % | Isobutene Selectivity % |
| --- | --- | --- | --- |
| 70 | 498 | 24.0 | 70 |
| 65 | 488 | 21.8 | 78 |
| 55 | 478 | 20.0 | 84 |
| 45 | 468 | 20.8 | 85 |
| 35 | 460 | 19.5 | 90 |
| 20 | 450 | 18.0 | 95 |

At high air concentrations, the catalyst bed temperature exceeded the furnace temperature and the major products were isobutene and carbon dioxide. As the concentration of air was lowered, the bed temperature decreased and the selectivity to isobutene improved. An optimum gas-composition was eventually achieved, which resulted in the bed temperature remaining at 450° C., whilst very little carbon dioxide was formed.

EXAMPLE 3

1%Pt-1%Sn/ZrO$_2$ (nominal composition, by mass) was prepared by the method described in Example 1 and Comparative Example 1, except that zirconia was substituted for γ-Al$_2$O$_3$. The catalyst was subjected to the same tests (at isobutane-GHSV=3000 hr$^{-1}$) as described in Example 1 and Comparative Example 1, except that both oxidative and direct dehydrogenation were carried out at 500° C. as well as 450° C.

TABLE 4

Direct Dehydrogenation Over 1% Pt—1% Sn/ZrO$_2$

| Elapsed Time/min | Isobutene Yield/% | |
| --- | --- | --- |
| | 450° C. | 500° C. |
| 2 | 15.7 | 29.2 |
| 25 | 15.2 | 25.7 |

TABLE 4-continued

Direct Dehydrogenation Over 1% Pt—1% Sn/ZrO$_2$

| Elapsed Time/min | Isobutene Yield/% | |
| --- | --- | --- |
| | 450° C. | 500° C. |
| 60 | 15.1 | 25.4 |
| 240 | 14.5 | 23.6 |
| 500 | — | 22.4 |
| 1150 | 13.4 | — |
| 1380 | 13.4 | 19.0 |
| 1500 | 13.4 | 18.6 |

The marked improvement at 500° C. can be seen.

In the oxidative mode, there was again a marked improvement at 500° C. compared to use at 450° C. At 500° C., the zirconia-containing catalyst showed improved durability over the 1%Pt-1%Sn/Al$_2$O$_3$ catalyst (Tables 2 and 5), with the isobutene yield exceeding 20% during the first 185 min of testing (compared to 150 min for Pt-Sn/Al$_2$O$_3$).

TABLE 5

Oxidative Dehydrogenation Over 1% Pt—1% Sn/ZrO$_2$

| Elapsed Time/min | Isobutene Yield/% | |
| --- | --- | --- |
| | 450° C. | 500° C. |
| 2 | 19.6 | 31.6 |
| 25 | 18.3 | 29.0 |
| 55 | 17.8 | 26.5 |
| 120 | 15.2 | 23.1 |
| 180 | 14.6 | 20.0 |
| 300 | 14.0 | 18.0 |

EXAMPLE 4 AND COMPARATIVE EXAMPLE 2

1%Pt-1%Sn/10%ZrO$_2$-Al$_2$O$_3$ (nominal composition, by mass) was prepared by the method described in Example 1 and Comparative Example 1, except that ZrO$_2$-Al$_2$O$_3$ was substituted for Al$_2$O$_3$. The mixed-oxide was made by impregnating γ-Al$_2$O$_3$ with an aqueous solution of zirconium nitrate, before drying (110° C.; air; 24 hr) and calcining (500° C.; air; 2 hr).

The good durability gained by using ZrO$_2$ (in Example 3) was lost by adding Al$_2$O$_3$. During oxidative testing (Example 4) at 500° C. under identical conditions to those of Example 3, the yield of isobutene dropped from 30.0% to 15.0% in the course of the first 85 min. This shows the deleterious effect of alumina; the catalyst does not have the present supporting amount of the mixture of tin oxide and zirconium oxide.

EXAMPLE 5

1%Pt/10%SnO$_2$-ZrO$_2$ (nominal composition, by mass) was prepared by co-precipitating SnO$_2$ and ZrO$_2$ from an aqueous mixture of tin(IV) chloride and hydrated zirconium oxychloride, using aqueous sodium hydroxide as the precipitant. The precipitate was washed thoroughly, before being dried (110° C.; air; 24 hr) and calcined (500° C.; air; 2 hr). The resultant mixed-oxide was impregnated with aqueous dinitrodiammine platinum(II), before the above drying and calcination steps were repeated. The catalyst was tested under the conditions described in Example 3.

The increased loading of Sn was not beneficial to direct dehydrogenation, but resulted in improved durability during oxidative dehydrogenation (compare Tables 5 and 6). At 500° C., the isobutene yield exceeded 20% during the first 210 minutes (compared to 185 minutes for 1%Pt-1%Sn/ZrO$_2$).

TABLE 6

Oxidative Dehydrogenation Over 1% Pt/10% SnO$_2$—ZrO$_2$

| Elapsed Time/min | Isobutene Yield/% | |
|---|---|---|
| | 450° C. | 500° C. |
| 2 | 17.1 | 28.2 |
| 25 | 18.4 | 28.7 |
| 55 | 18.2 | 27.6 |
| 120 | 16.5 | 24.2 |
| 180 | 14.8 | 21.3 |
| 240 | — | 18.7 |

EXAMPLE 6

1%Pt/20%SnO$_2$-ZrO$_2$ (nominal composition, by mass) was prepared by the method described in Example 5, and tested under the conditions described in Example 3. Again, the clearest benefit derived from the high tin loading was apparent in the oxidative mode, both at 450° C. and 500° C., when the rate of deactivation was even further reduced (compare Tables 5, 6 and 7). In particular, the durability at 450° C. (as measured by the duration of yield ≧15%) exceeded 24 hr (compared to 6 hr for 1% Pt-1%Sn/Al$_2$O$_3$); see FIG. 1.

TABLE 7

Oxidative dehydrogenation over 1% Pt/20% SnO$_2$—ZrO$_2$

| Elapsed Time/min | Isobutene Yield/% | |
|---|---|---|
| | 450° C. | 500° C. |
| 2 | 19.0 | 38.7 |
| 25 | 18.8 | 31.4 |
| 55 | 18.6 | 29.0 |
| 180 | 18.0 | 24.0 |
| 300 | 17.6 | 20.8 |
| 400 | — | 18.8 |
| 1260 | 15.1 | — |
| 1500 | 14.9 | — |

EXAMPLE 7

A fresh sample of 1%Pt/20%SnO$_2$-ZrO$_2$ (as described in Example 6) was treated under oxidative conditions, but at half the space velocity used in Examples 1–6 and Comparative Examples 1 and 2.

Figure 2:
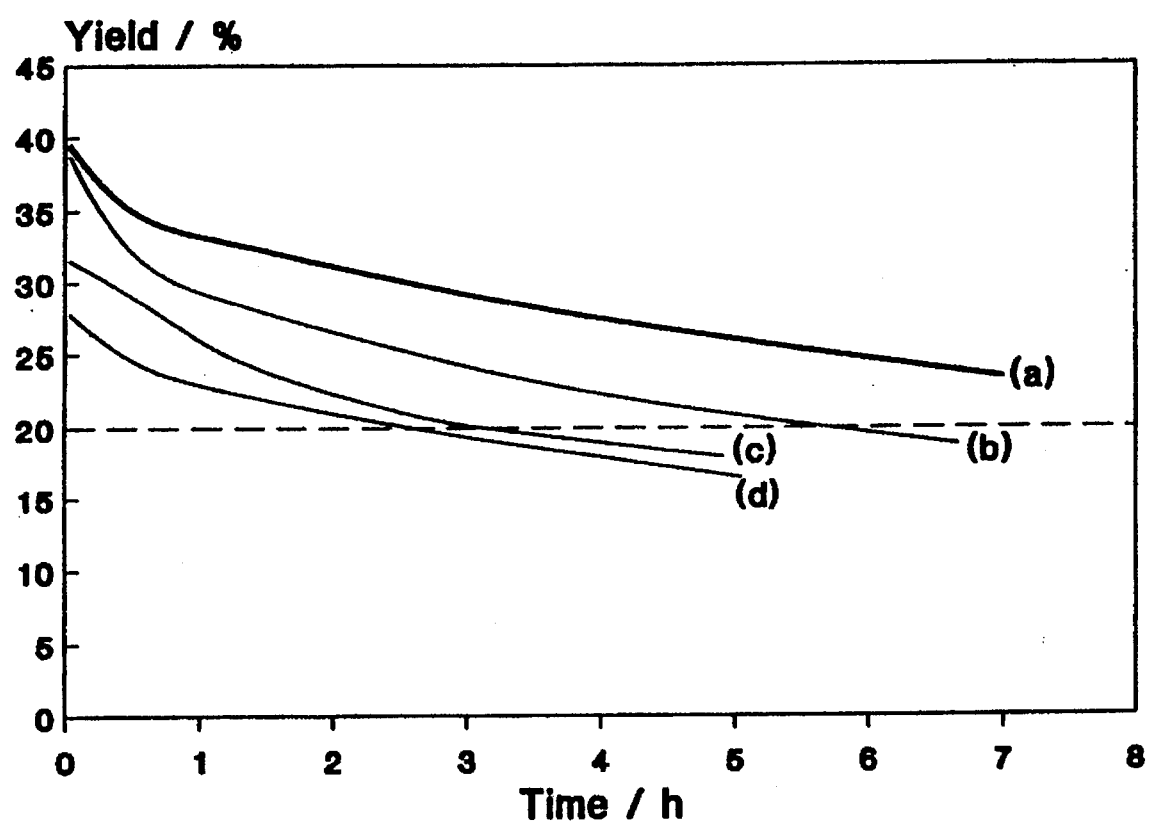

At this lower space velocity (isobutane-GHSV=1500 hr$^{-1}$), the catalyst de-activated more gradually. As FIG. 2 shows, its initial activity at 500° C. was similar to that observed in Example 6, but the yield still exceeded 25% after 5 hours (the time taken for the yield to fall below 20% at isobutane-GHSV =3000 hr$^{-1}$).

COMPARATIVE EXAMPLE 3

1%Pt/SnO$_2$ (nominal composition, by mass) was prepared by impregnating SnO$_2$ with an aqueous solution of tetraammineplatinum(II) hydroxide, before drying (110° C.; air; 24 hr) and calcining (500° C.; air; 2 hr). It was tested under the conditions described in Example 3. This material was a very poor catalyst for both direct dehydrogenation (2.0% maximum yield at 450° C.) and oxidative dehydrogenation (3.2% maximum yield at 450° C.).

EXAMPLE 8

The ability of 1%Pt/20%SnO$_2$-ZrO$_2$ (as described in Example 6) to dehydrogenate linear alkanes was tested by following the procedures given in Example 3, but replacing the isobutane reactant with normal butane. During direct dehydrogenation, the initial total yield of unsaturated products was 26% (product selectivity: 32% 1-butene, 27% cis 2-butene, 38% trans 2-butene, 2% butadiene), but declined to 14% in the space of 3 hours. On switching to the oxidative mode, without first regenerating the catalyst in any way, the total yield recovered, reaching a maximum of 29% before declining slowly (down to 25% after a further 2 hours); the product distribution was very similar to that observed during direct dehydrogenation.

EXAMPLE 9

The sequence of tests described in Example 8 was repeated using propane as the alkane reactant. During direct dehydrogenation, the initial yield of propene was 19%; after 3 hours, it had declined to 12% On switching to the oxidative mode, the yield was restored to 19%. Thereafter, it declined slowly to 17% during the next 4 hours.

The invention is further illustrated by the yield data given graphically for various catalysts in the accompanying FIGS. 1 and 2.

FIG. 1:

Oxidative dehydrogenation of isobutane (GHSV=3000 hr$^{-1}$) at 450° C., over (a) 1%Pt/20%SnO$_2$-ZrO$_2$;
(b) 1%Pt-1%Sn/Al$_2$O$_3$.

FIG. 2:

Oxidative dehydrogenation of isobutane at 500° C., over (a) 1%Pt/20%SnO$_2$-ZrO$_2$;
(b) 1%Pt/20%SnO$_2$-ZrO$_2$;
(c) 1%Pt-1%Sn/ZrO$_2$;
(d) 1%Pt-1%Sn/Al$_2$O$_3$.

For (a), GHSV=1500 hr$^{-1}$; (b)–(d); GHSV=3000 hr$^{-1}$

We claim:

1. A catalyst for alkane dehydrogenation, comprising by weight 0.1 to 3% platinum, calculated as metal, 6 to 60% tin oxide, and 37 to 94.9% zirconium oxide, the platinum deposited upon a support which is a mixture of the tin oxide and the zirconium oxide.

2. A catalyst according to claim 1, containing 10 to 60% by weight of the tin oxide.

3. A catalyst according to claim 1, wherein the support contains substantially no alumina.

4. A catalyst according to claim 1, consisting essentially of 0.1 to 3% by weight of platinum, calculated as metal, 10 to 60% by weight of tin oxide, 37 to 94.9% zirconium oxide, and at least one member selected from the group consisting of stabilisers and promoters.

5. A catalyst according to claim 1, wherein the support comprises SnO$_2$ and ZrO$_2$ in a weight ratio of approximately 1:4.

6. A catalyst according to claim 5, comprising approximately 1% by weight of platinum, impregnated onto a co-precipitate of $SnO_2$ and $ZrO_2$ in a weight ratio of approximately 1:4.

7. A catalyst according to claim 1, wherein the catalyst has substantially an absence of alumina.

8. A catalyst according to claim 1, wherein the catalyst contains 15–30% by weight of tin oxide.

9. A catalyst according to claim 1, wherein the catalyst contains 70–85% by weight zirconium oxide.

10. A catalyst according to claim 1, wherein the catalyst has a weight ratio of the tin oxide to the zirconium oxide of 1:3-9.

11. A catalyst according to claim 1, wherein the catalyst has a weight ratio of the tin oxide to the zirconium oxide of 1:3-5.

* * * * *